United States Patent
Lin et al.

(10) Patent No.: US 8,007,726 B2
(45) Date of Patent: Aug. 30, 2011

(54) MICROARRAY BIOPROBE DEVICE INTEGRATED WITH AN AMPLIFIER HAVING BOTTOM-GATE THIN FILM TRANSISTORS

(75) Inventors: Jium-Ming Lin, Hsinchu (TW); Li-Chern Pan, Taipei (TW); Po-Wei Lin, Taipei (TW)

(73) Assignee: Chung Hua University, Hsin Chu (TW)

( * ) Notice: Subject to any disclaimer, the term of this patent is extended or adjusted under 35 U.S.C. 154(b) by 1121 days.

(21) Appl. No.: 11/806,786

(22) Filed: Jun. 4, 2007

(65) Prior Publication Data
US 2008/0297135 A1 Dec. 4, 2008

(51) Int. Cl.
*G01N 27/00* (2006.01)
*G01N 7/00* (2006.01)
*G01N 15/06* (2006.01)

(52) U.S. Cl. ... 422/82.01; 422/50; 422/68.1; 422/82.02; 600/372; 600/373; 600/377; 600/393

(58) Field of Classification Search .......... 422/50, 422/68.1, 82.01, 82.02; 600/372, 373, 377, 600/393
See application file for complete search history.

(56) References Cited

U.S. PATENT DOCUMENTS

| | | | |
|---|---|---|---|
| 4,969,468 A | 11/1990 | Byers et al. | |
| 7,212,851 B2* | 5/2007 | Donoghue et al. | 600/544 |
| 7,548,775 B2* | 6/2009 | Kipke et al. | 600/378 |
| 7,645,262 B2* | 1/2010 | Greenberg et al. | 604/115 |
| 7,805,175 B2* | 9/2010 | Lin et al. | 600/393 |
| 2004/0006264 A1* | 1/2004 | Mojarradi et al. | 600/378 |
| 2009/0318824 A1 | 12/2009 | Nishida et al. | |

* cited by examiner

*Primary Examiner* — Brian J Sines
(74) *Attorney, Agent, or Firm* — Birch, Stewart, Kolasch & Birch, LLP

(57) ABSTRACT

The present invention provides a microarray bioprobe device integrated with an amplifier having bottom-gate thin film transistors. The present invention utilizes a micro-electro-mechanical process as well as a semiconductor process to integrate microarray bioprobes and an amplifier having bottom-gate thin film transistors on a flexible substrate. As such, a signal obtained by the microarray bioprobes can be amplified nearby to improve the signal-to-noise ratio and impedance matching. The microarray bioprobes are formed on the flexible substrate such that the present microarray bioprobe device can be disposed to conform to the profile of a living body's portion so as to improve electrical contact between the bioprobes and the living body's portion.

19 Claims, 6 Drawing Sheets

MICROARRAY BIOPROBE DEVICE INTEGRATED WITH AN AMPLIFIER HAVING BOTTOM-GATE THIN FILM TRANSISTORS

BACKGROUND OF THE INVENTION

1. Field of the Invention

The present invention relates to a microarray bioprobe device integrated with an amplifier having bottom-gate thin film transistors, and more practically, to a microarray bioprobe device integrated with an amplifier having bottom-gate thin film transistors on a flexible substrate by Micro-Electro-Mechanical System (MEMS) processes and semiconductor processes.

2. Description of Related Art

Conventional micro array biological probes are produced on a hard silicon wafer substrate. The product is not only heavy and frangible but also high temperature processes needed. The manufacture cost is expensive. Moreover, the conventional micro array biological probes fail to be designed and disposed relying on the profile of a living body's portion, and adversely affecting contact between the biological probes and living body. Besides, after a signal detected from the conventional micro array biological probes, the signal is picked up to be processed so as to improve signal-to-noise ratio and impedance matching. Additional devices for signal processing are required. Thus, the manufacture cost of the conventional micro array probes requires more, and the manufacturing complexity is high. Although the signal-to-noise ratio and impedance matching can be improved by integrating the conventional micro array biological probes and a transistor amplifier for signal processing together, both of them are produced on a hard silicon wafer substrate, and thus the product still fails to be designed and disposed relying on the profile of the living body's portion.

Although the conventional micro array biological probe element is produced on a flexible substrate, it can be designed and disposed relying on the profile of the living body's portion to increase the contact effect between the biological probes and living body. However, in view of the current technology, the conventional micro array biological probes and the transistor amplifier can not be integrated together to obtain better results of signal processing for facilitating further analysis and determination. The reason is that high temperature is required in the manufacture process of the transistor amplifier, and the flexible substrate will be deformed at such high temperature. As such, it is difficult to produce the transistor amplifier on the flexible substrate.

For the current micro array biological probe technology, there is lack of a micro array biological probe element capable of mass-production, cost efficiency, being designed and disposed relying on the profile of the living body's portion, and also improving the signal-to-noise ratio and impedance matching.

SUMMARY OF THE INVENTION

The objective of the present invention is to provide a microarray bioprobe device integrated with an amplifier having bottom-gate thin film transistors, which integrates micro array biological probes and thin film transistors on a flexible substrate by Micro-Electro-Mechanical System (MEMS) processes and semiconductor processes to improve the contact between the probes and the living body and also the signal-to-noise ratio.

To achieve the objective, a microarray bioprobe device integrated with an amplifier having bottom-gate thin film transistors of the present invention includes a first flexible substrate, a second flexible substrate, a plurality of biological probes and at least one an amplifier having bottom-gate thin film transistors. The first flexible substrate has a plurality of first conducting wires formed therein, by which electrical transmission is generated between a first and second surfaces of the first flexible substrate. The biological probes are formed on the first surface of the first flexible substrate, and each of the biological probes respectively electrically connects with one of the conducting wires corresponding thereto. The second flexible substrate has a plurality of second conducting wires formed therein, and by which an electrical transmission is generated between an upper and lower surfaces of the second flexible substrate, and the lower surface of the second flexible substrate is electrically jointed to the second surface of the first flexible substrate. The at least one transistor amplifier and a plurality of lead wires are formed on the upper surface of the second flexible substrate, wherein each of the lead wires is respectively electrically connected with one of the second conducting wires corresponding thereto. The microarray bioprobe device integrated with the amplifier having bottom-gate thin film transistors of the present invention makes electrical signals transmitted between the biological probes and the amplifier having bottom-gate thin film transistors by the first conducting wires, second conducting wires and the lead wires.

On the other hand, the biological probe has a tip end to facilitate thrusting into the living body to decrease the contact impedance. The present invention can vary a density and occupied areas of the probes as well as sharpness of the tip ends thereof to change the contact impedance so as to meet different needs.

The present invention can integrate the micro array biological probes and amplifier having bottom-gate thin film transistors together on the flexible substrate such that the product of the present invention can be designed for roll-to roll types to facilitate mass-production.

DETAILED DESCRIPTION OF THE PREFERRED EMBODIMENTS

The present invention employs the MEMS process and semiconductor process to integrate an amplifier having bottom-gate thin film transistors and micro array biological probes on the flexible substrate. It becomes possible to dispose the microarray bioprobe device in conformity with the profile of the living body's portion by forming the microarray bioprobe device on the flexible substrate. As such, the contact effect between the biological probes and living body becomes better. On the other hand, because the amplifier having bottom-gate thin film transistors is also produced on the flexible substrate, a signal detected from the biological probes can be amplified through a short path. The signal-to-noise ratio and impedance matching can be improved, and the cost of manufacture is decreased.

The microarray bioprobe device integrated with the amplifier having bottom-gate thin film transistors of the present invention will be described in detail in the following according to preferred embodiments and accompanying drawing.

Figure 1A:
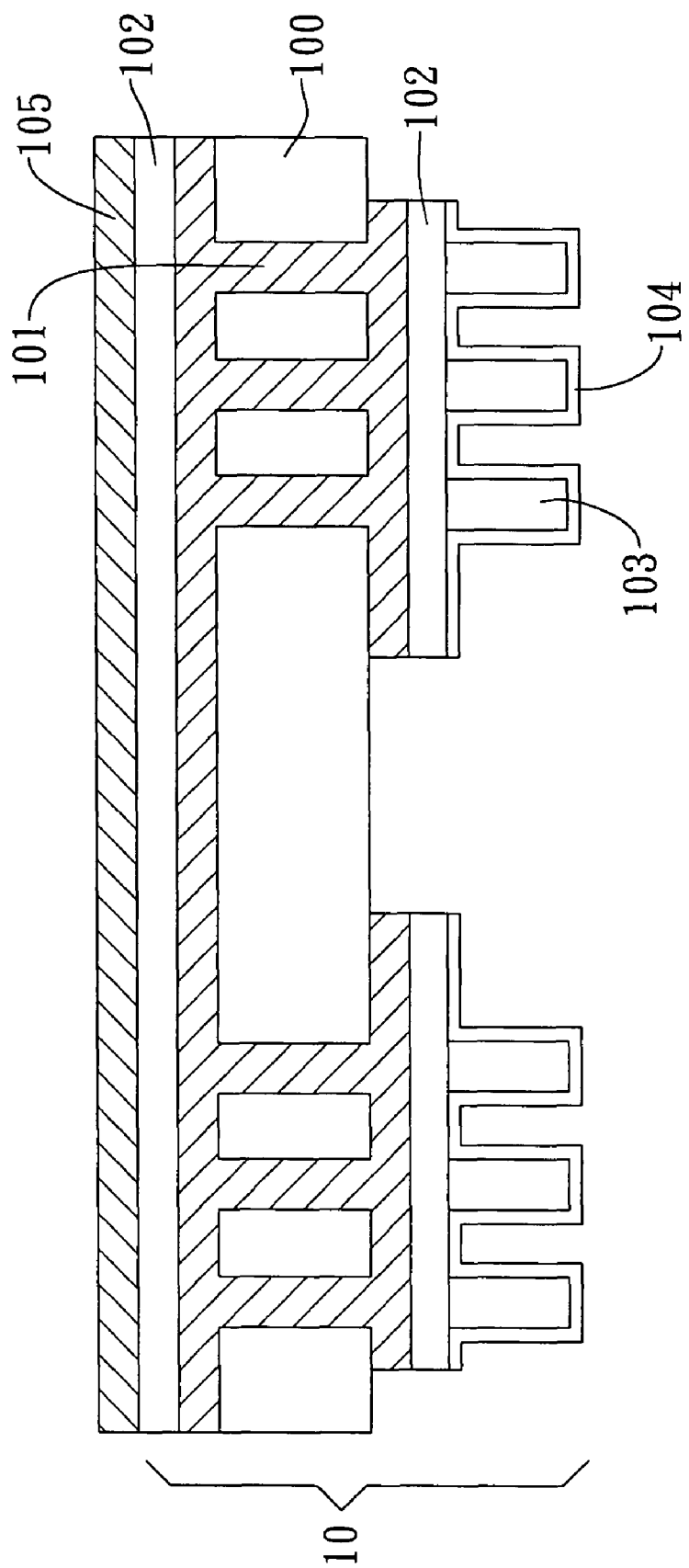
FIG. 1A is a schematic cross-sectional view of a microarray bioprobe device according to a first embodiment of the present invention.
Figure 2A:
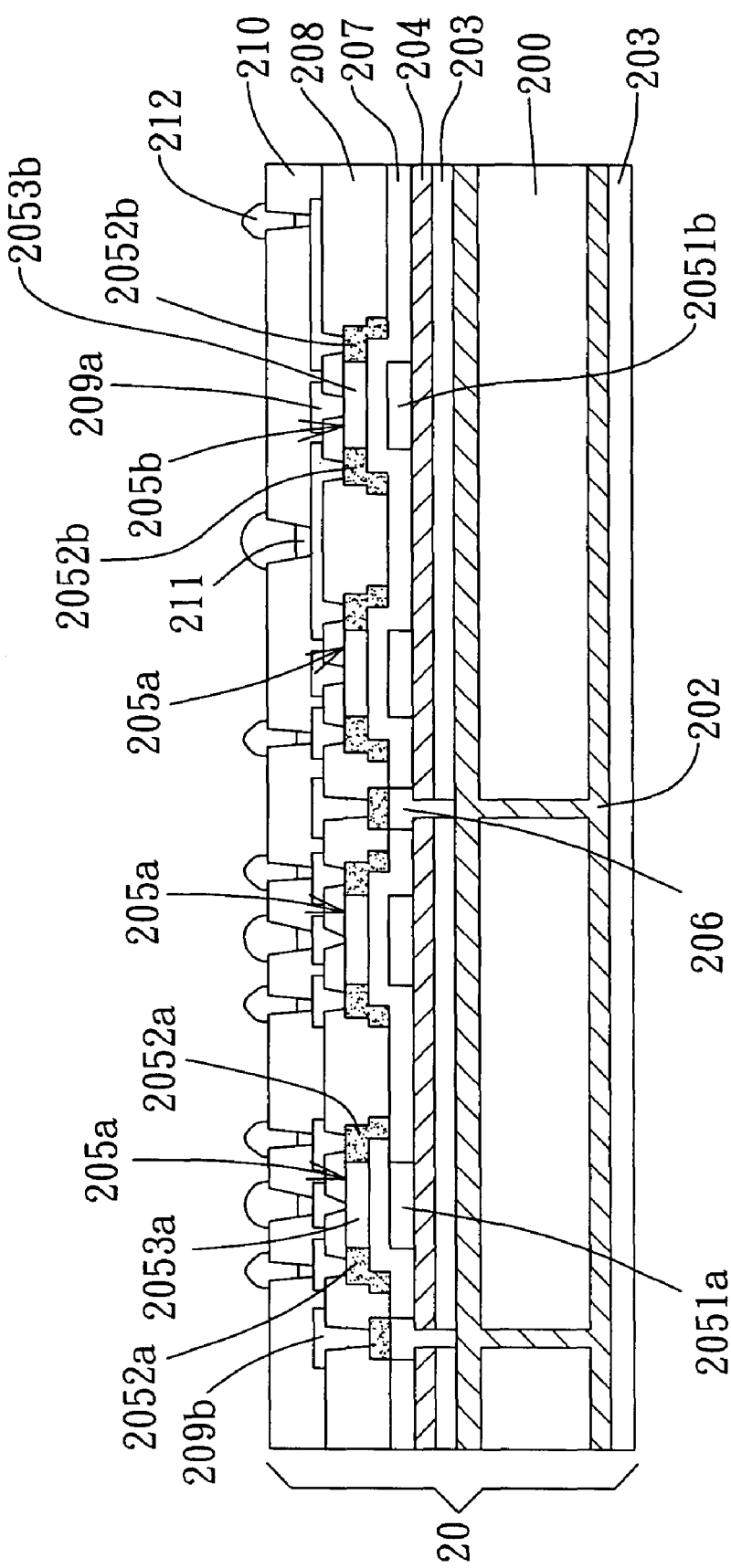
FIG. 2A is a schematic cross-sectional view of an amplifier having bottom-gate thin film transistors of the present invention.
Figure 2B:
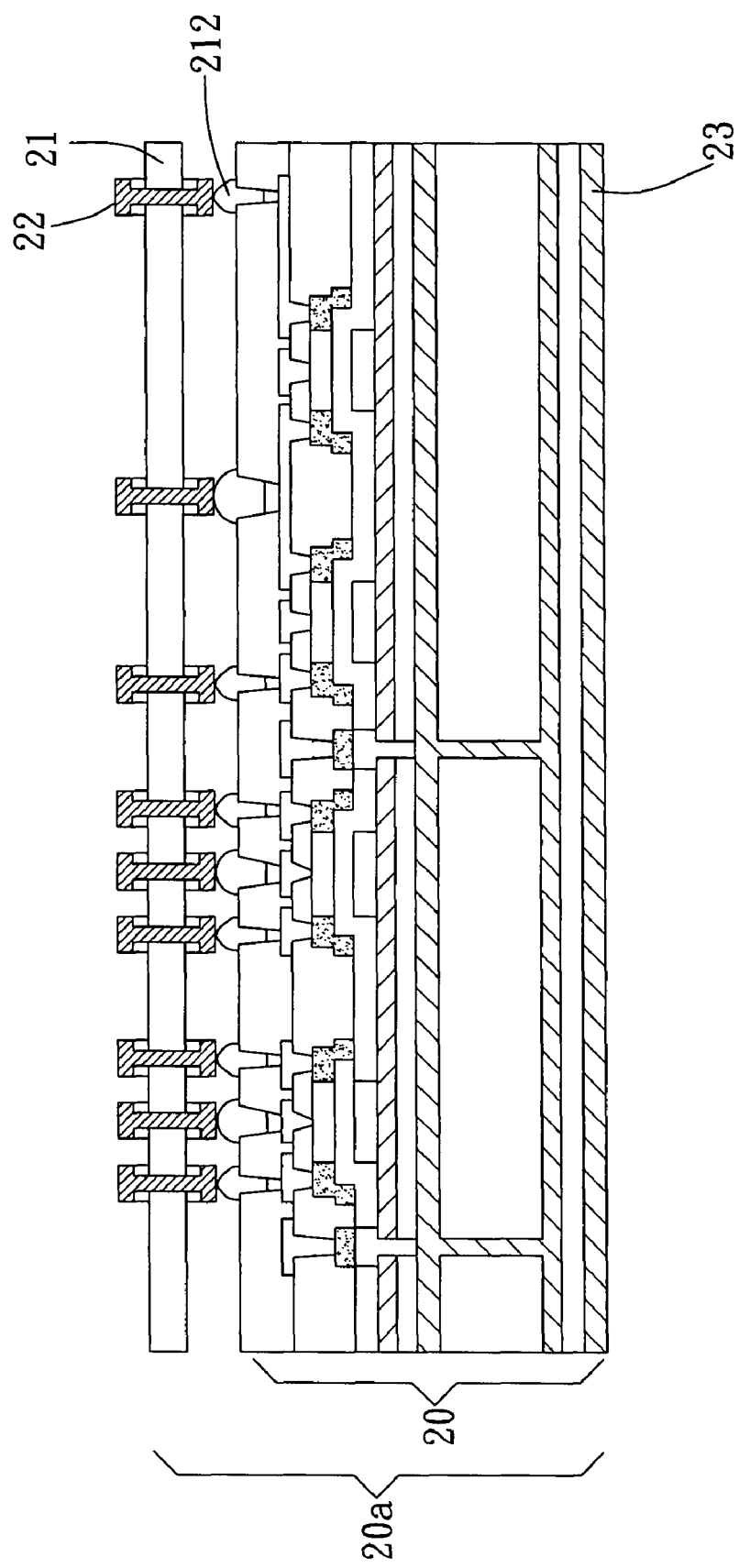
FIG. 2B is a schematic cross-sectional view of an integrated module of the amplifier having bottom-gate thin film transistors of FIG. 2A and an interface.
Figure 3:
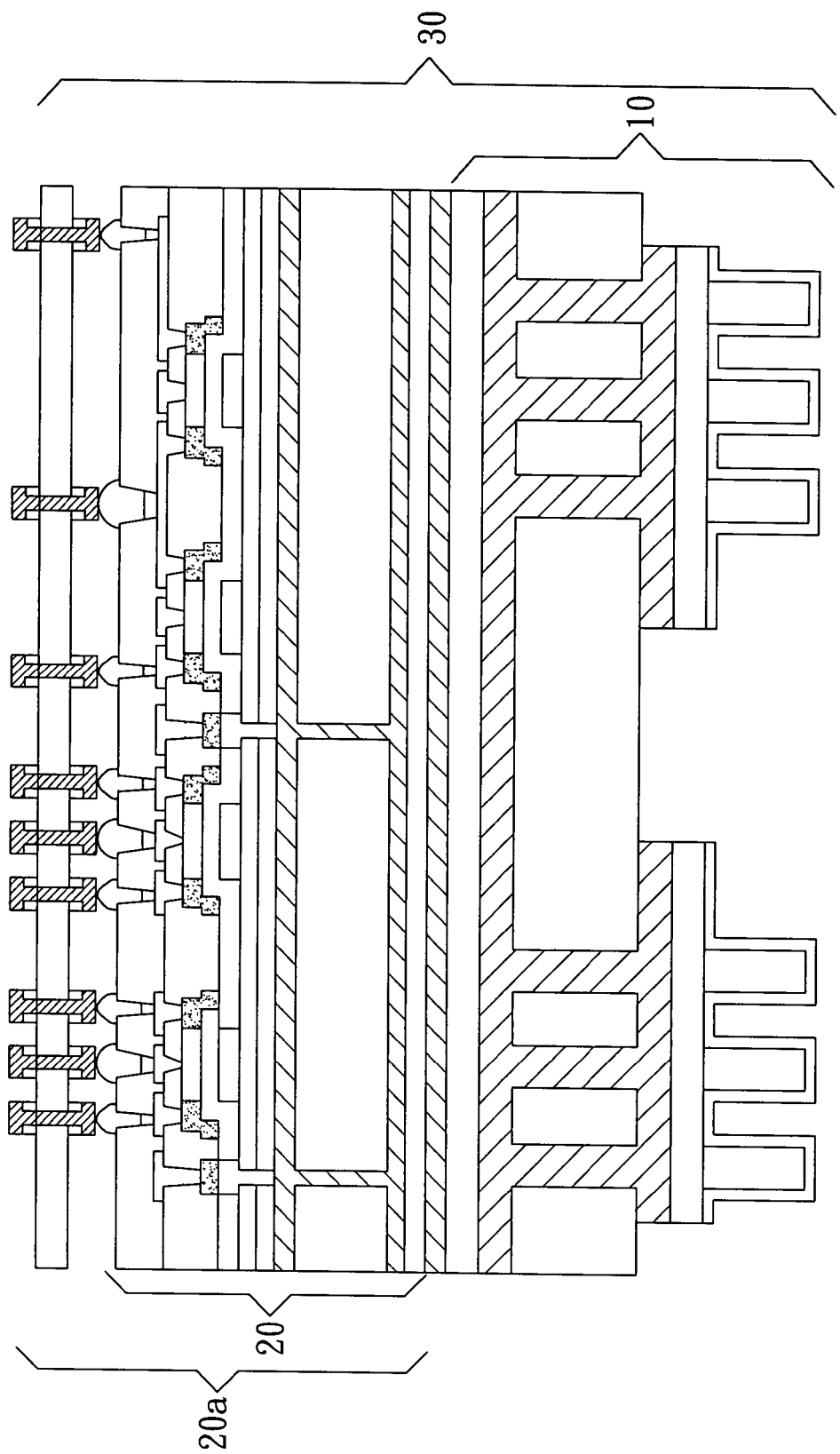
FIG. 3 is a schematic cross-sectional view of a microarray bioprobe device integrated with the amplifier having bottom-gate thin film transistors of the present invention.

FIG. 3 is a schematic cross-sectional view of a microarray bioprobe device 30 integrated with an amplifier having bottom-gate thin film transistors according to a preferred embodiment of the present invention. The microarray bioprobe device 30 integrated with the amplifier having bottom-gate thin film transistors comprises a micro array biological probe element 10 and an integrated module 20a of the amplifier having bottom-gate thin film transistors and an interface. FIG. 1A is a schematic cross-sectional view of the micro array biological probe element 10. FIG. 2A is a schematic cross-sectional view of the amplifier having bottom-gate thin film transistors 20, and FIG. 2B is a schematic cross-sectional view of the integrated module 20a of the amplifier having bottom-gate thin film transistors and the interface. Referring to FIG. 1A, the microarray biological probe element 10 comprises: a first flexible substrate 100, such as a flexible plastic substrate; a plurality of first conducting wires 101 passing through the first flexible substrate 100 to establish electrical connection between a first and second surfaces of the first flexible substrate 100, and the first conducting wires 101 can be formed of titanium or titanium nitride; a first conducting seeding layer 102 formed respectively on a first surface and a second surface of the first flexible substrate 100 in electrical connection with the first conducting wires 101, and the first conducting seeding layer 102 can be formed of copper, nickel or gold; a microarray biological probe module comprising a plurality of groups of array-typed biological probes 103 formed on a lower side of the first conducting seeding layer 102 of the first surface of the first flexible substrate 100, and each of the array-typed biological probes 103 electrically connects with one of the first conducting wires 101 corresponding thereto; and a biological compatible conducting layer 104 covering the array biological probe module to be as an interface layer of the array-typed biological probes 103 for contacting the living body, and the biological compatible conducting layer 104 can be formed of titanium, titanium nitride or other biological compatible metals having high hardness, with a thickness of 1 to 5 µm, generally a thickness of 2 µm. In addition, the backside of the microarray biological probe element 10 is placed with a layer of conductive glue (such as silver glue) 105 or solder paste so as to facilitate the following back-to-back joint with the integrated module 20a of the amplifier having bottom-gate thin film transistors and the interface.

Figure 1B:
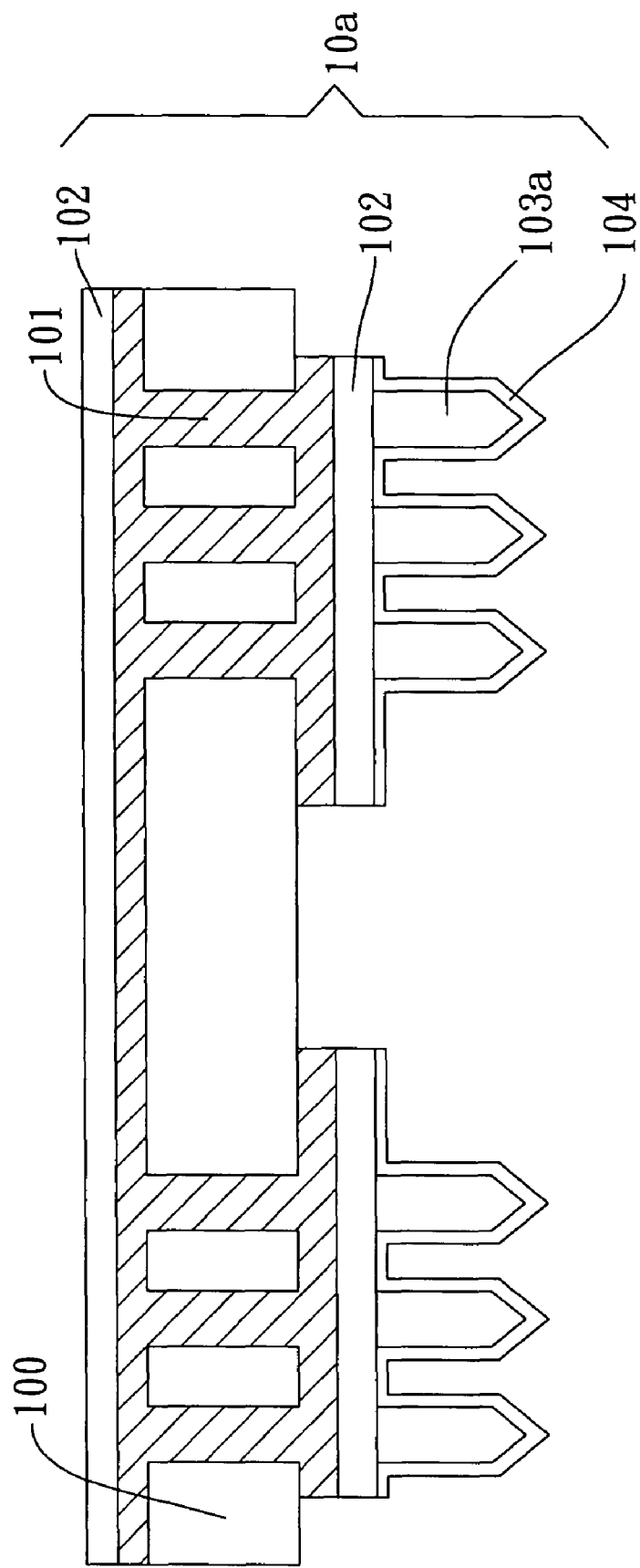
FIG. 1B is a schematic bottom view of a microarray bioprobe device according to another embodiment of the present invention.

FIG. 1B is a schematic cross-sectional view of the microarray bioprobe device according to another preferred embodiment of the present invention. The only difference between this preferred embodiment and that of FIG. 1A is that each of biological probes 103a has a tip end for facilitating thrusting into the living body to decrease the contact impedance, and it is suitable for high-current signal input and output.

On the other hand, the present invention can change a density and occupied areas of the biological probes as well as sharpness of the tip ends thereof so as to change the impedance for meeting different needs.

Figure 4:
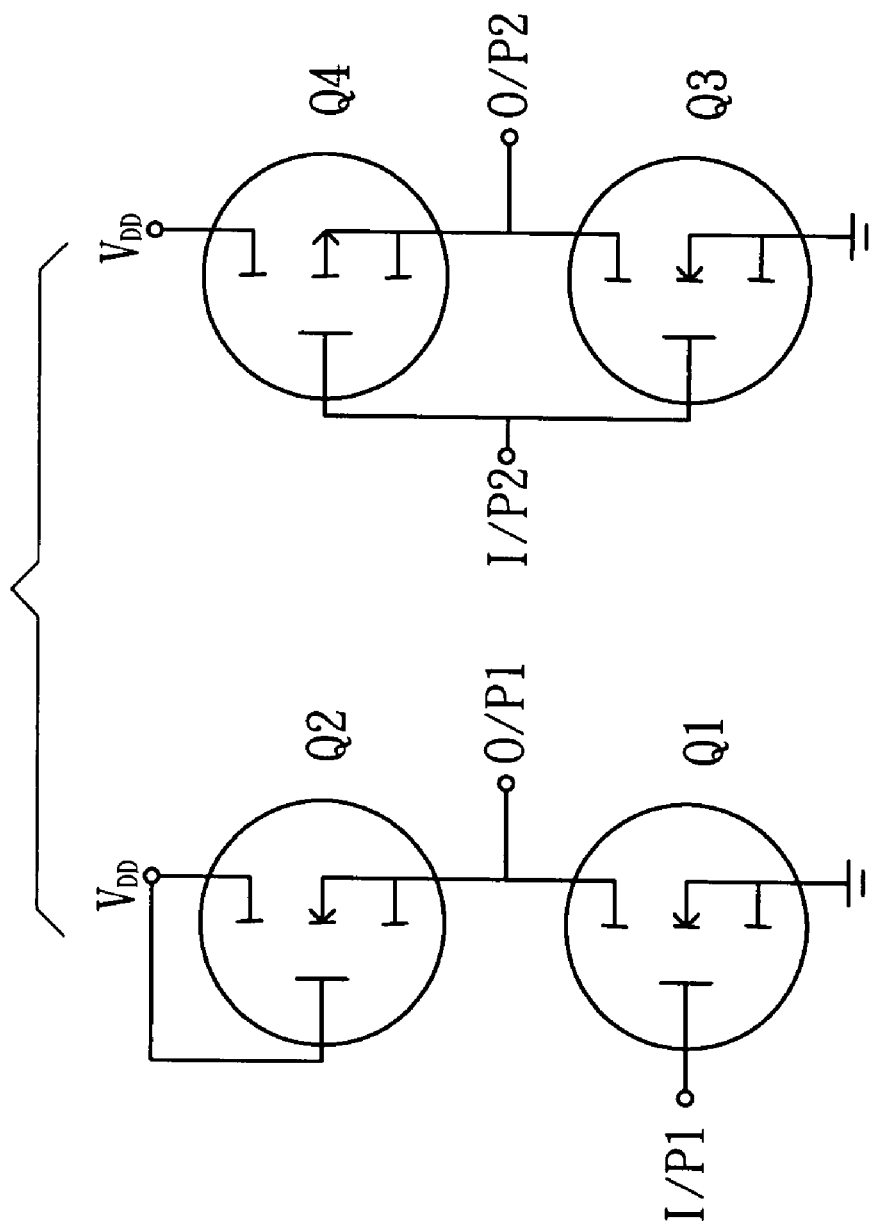
FIG. 4 is a schematic circuit of an inverting amplifier of the present invention.

Referring to FIG. 2A, the amplifier having bottom-gate thin film transistors 20 of the present invention comprises: a second flexible substrate 200, for example a flexible plastic substrate; a plurality of second conducting wires 202 passing through the second flexible substrate 200 to transmit electrical signals between two surfaces thereof, and the second conducting wires 202 can be formed of a conducting seeding layer such as titanium, titanium nitride or other metals with high hardness and high adhesiveness; a second conducting layer 203, such as a copper layer, is formed on the second conducting wires 202 of the upper surface of the second flexible plastic substrate 200 and on the second conducting wires 202 of the lower surface of the second flexible plastic substrate 200; a first dielectric layer 204, such as a silicon dioxide ($SiO_2$) layer, a silicon nitride ($Si_3N_4$) layer or other insulating layers, formed on the second conducting layer 203 of the upper surface of the second flexible substrate 200; at least three first electrical conductive type bottom-gate thin film transistors 205a (for example, N-channel bottom-gate thin film transistors) and at least one second electrical conductive type bottom-gate thin film transistors 205b (for example, P-channel bottom-gate thin film transistor) and a plurality of lead wires 206 are formed on the first dielectric layer 204, and the lead wires 206 passes through the first dielectric layer 204 and the second conducting layer 203, and respectively electrically connecting with one of the second conducting wires 202 corresponding thereto, each of the three first electrical conductive type bottom-gate thin film transistors 205a includes a bottom gate 2051a formed on the first dielectric layer 204, a pair of first electrical conductive type source/drain 2052a and a first electrical conductive type channel 2053a formed on the bottom-gate 2051a, and a second dielectric layer 207, for example, a silicon dioxide ($SiO_2$) layer or a silicon nitride ($Si_3N_4$) layer or other insulating layer is formed among the bottom-gate 2051a, the first electrical conductive type source/drain 2052a and the first electrical conductive type channel 2053a in order to be provided as a gate insulating layer of the first electrical conductive type bottom-gate thin transistors 205a, and the bottom gate 2051a can be made of aluminum, chromium, nickel or other metals. Similarly, the second electrical conductive type bottom-gate thin film transistors 205b comprises a bottom-gate 2051b formed on the first dielectric layer 204, a pair of second electrical conductive type source/drain 2052b and a first electrical conductive type channel 2053b formed on the bottom-gate 2051b, and the second dielectric layer 207 is also formed among the second bottom gate 2051b, the second electrical conductive type source/drain 2052b and the second electrical conductive type channel 2053b in order to be provided as a bottom-gate insulating layer of the second electrical conductive type bottom-gate thin film transistor 205b, wherein the three first electrical conductive type bottom-gate thin film transistors 205a and the second electrical conductive type bottom-gate thin film transistors 205b form the amplifier having bottom-gate thin film transistors of the present invention, which constitutes two inverting amplifiers whose schematic circuit is shown as FIG. 4; a third dielectric layer 208, for example, a silicon nitride ($Si_3N_4$) layer, a silicon dioxide ($SiO_2$) layer or other insulating layers, is formed on the first electrical conductive type thin film transistor 205a, the second electrical conductive type thin film transistor 205b and the lead wire 206; a plurality of third conducting wires 209a and a plurality of first pads 209b are formed in via holes of the third dielectric layer 208 and on the surface thereof, and the third conducting wires 209a is connected with the first electrical conductive type source/drain 2052a and the first electrical conductive type channel 2053a of the first electrical conductive type channel bottom-gate thin film transistors 205a and the second electrical conductive type source/drain 2052b and the second electrical conductive type channel 2053b of the second electrical conductive type channel bottom-gate thin film transistors 205b, and the first pads 209b is connected with the lead wires 206, wherein the third conducting wires 209a and the first pads 209b can be aluminum or other metals; an insulating protecting layer 210 formed on the third conducting wires 209a and the first pads 209b so as to isolate humidity and protect the thin film transistors underneath, and the protecting layer 210 can be a silicon dioxide ($SiO_2$) layer, a silicon nitride ($Si_3N_4$) layer or other insulating layers; a plurality of second pads 211 is respectively formed in each of through holes of the protecting layer 210, wherein the second pads 211, which can be made of nickel (Ni), gold, or other metals, are respectively formed on the third conducting wire 209a; and a plurality of conducting bumps 212, which can be made of conductive glue or solder paste, is formed on the second pads 211, to facilitate establishing electrical connection with the interface plate for power supply, ground and input/output (electrical connectors such as BNC connectors are formed on a backside thereof).

Referring to FIG. 2B, the integrated module 20a of the amplifier having bottom-gate thin film transistors and the interface of the present invention comprises an interface plate 21 having power, ground and input/output electrical connectors 22 and the amplifier having bottom-gate thin film transistors 20. The interface plate 21 is a flexible substrate and the electrical connectors 22 are made of conductive glue or solder paste and penetrate the interface plate 21. Each of the conducting bumps 212 of the amplifier having bottom-gate thin film transistors 20 corresponds to one of the electrical connectors 22 so that the conducting bumps 212 are aligned and jointed to the electrical connectors 22 to form the integrated module 20a of the amplifier having bottom-gate thin film transistors and the interface. Then, a layer of conductive glue 23, (such as sliver glue) or solder paste, is placed on the backside of the integrated module 20a of the amplifier having bottom-gate thin film transistors and the interface to facilitate the following back-to-back joint with the microarray biological probe element 10.

Referring to FIG. 3, for the microarray bioprobe device 30 integrated with the amplifier having bottom-gate thin film transistors of the present invention, the integrated module 20a of the amplifier having bottom-gate thin film transistors and the interface and the microarray biological probe element 10 are coated with the conductive glue or solder paste on the backside and jointed together by back-to-back so as to form the microarray bioprobe device 30 integrated with the amplifier having bottom-gate thin film transistors Moreover, because the silver glue can be soften and then separated from where it is coated after heating with the temperature lower than the glass transition temperature of the flexible substrate, it facilitates to replace the micro array biological probe element 10 by using the silver glue as the joint agent. The maintenance fee of the microarray bioprobe device 30 integrated with the amplifier having bottom-gate thin film transistors of the present invention can be decreased.

On the other hand, the sliver glue can be replaced by a double-sided conducting film or a double-sided conducting tape to joint the integrated module 20a of the amplifier having bottom-gate thin film transistors and the interface and the micro array biological probe element 10.

The present invention integrates the microarray biological probe element and the amplifier having bottom-gate thin film transistors on the flexible substrate such that the product of the present invention can be designed for roll-to-roll type, and facilitating mass-production.

While the invention has been described by way of examples and in terms of preferred embodiments, it is to be understood that those who are familiar with the subject art can carry out various modifications and similar arrangements and procedures described in the present invention and also achieve the effect of the present invention. Hence, it is to be understood that the description of the present invention should be accorded with the broadest interpretation to those who are familiar with the subject art, and the invention is not limited thereto.

What is claimed is:

1. A microarray bioprobe device integrated with an amplifier having bottom-gate thin film transistors comprising:
    a first flexible substrate having a plurality of first conducting wires formed therein, by which electrical transmission is generated between a first and second surfaces of said first flexible substrate;
    a plurality of biological probes formed on said first surface of said first flexible substrate, each of said biological probes electrically connecting with corresponding one of said conducting wires respectively;
    a second flexible substrate having a plurality of second conducting wires formed therein, by which an electrical transmission is generated between an upper and lower surfaces of said second flexible substrate, and said lower surface of said second flexible substrate is electrically jointed to said second surface of said first flexible substrate; and
    at least one amplifier having bottom-gate thin film transistors and a plurality of lead wires formed on said upper surface of said second flexible substrate, wherein each of said lead wires is electrically connected with corresponding one of said second conducting wires respectively;
    wherein each said bottom-gate thin film transistor comprises a bottom gate formed on said upper surface of said second flexible substrate, a pair of source/drain and a channel formed above said bottom-gate, electrical signals are transmitted between said biological probes and said amplifier having bottom-gate thin film transistors by said first conducting wires, said second conducting wires and said lead wires.

2. The microarray bioprobe device integrated with an amplifier having bottom-gate thin film transistors of claim 1, wherein said biological probes are arranged as a plurality of arrays.

3. The microarray bioprobe device integrated with an amplifier having bottom-gate thin film transistors of claim 1, wherein each said biological probe has a tip end.

4. The microarray bioprobe device integrated with an amplifier having bottom-gate thin film transistors of claim 1, further comprising an insulating protecting layer covering said amplifier having bottom-gate thin film transistors and said lead wires.

5. The microarray bioprobe device integrated with an amplifier having bottom-gate thin film transistors of claim 3, further comprising an insulating protecting layer covering said amplifier having bottom-gate thin film transistors and said lead wires.

6. The microarray bioprobe device integrated with an amplifier having bottom-gate thin film transistors of claim 1, further comprising an interface plate for power supply, ground and input/output electrically connected with said amplifier having bottom-gate thin film transistors.

7. The microarray bioprobe device integrated with an amplifier having bottom-gate thin film transistors of claim 3, further comprising an interface plate for power supply, ground and input/output electrically connected with said amplifier having bottom-gate thin film transistors.

8. The microarray bioprobe device integrated with an amplifier having bottom-gate thin film transistors of claim 1, wherein said biological probe is formed of nickel, chromium or other metals with high hardness and high adhesiveness.

9. The microarray bioprobe device integrated with an amplifier having bottom-gate thin film transistors of claim 8, wherein said biological probe has a covering layer formed of titanium (Ti), titanium nitride (TiN) or other biological compatible metal with high hardness.

10. The microarray bioprobe device integrated with an amplifier having bottom-gate thin film transistors of claim 3, wherein said biological probe is formed of nickel, chromium or other metals with high hardness and high adhesiveness.

11. The microarray bioprobe device integrated with an amplifier having bottom-gate thin film transistors of claim 10, wherein said biological probe has a covering layer formed of titanium (Ti), titanium nitride (TiN) or other biological compatible metal with high hardness.

12. The microarray bioprobe device integrated with an amplifier having bottom-gate thin film transistors of claim 1, wherein said second flexible substrate and said first flexible substrate are jointed by electrical conductive glue or solder paste.

13. The microarray bioprobe device integrated with an amplifier having bottom-gate thin film transistors of claim 3, wherein said second flexible substrate and said first flexible substrate are jointed by electrical conductive glue or solder paste.

14. The microarray bioprobe device integrated with an amplifier having bottom-gate thin film transistors of claim 12, wherein said electrical conductive glue is sliver glue.

15. The microarray bioprobe device integrated with an amplifier having bottom-gate thin film transistors of claim 13, wherein said electrical conductive glue is sliver glue.

16. The microarray bioprobe device integrated with an amplifier having bottom-gate thin film transistors of claim 1, wherein said amplifier comprises at least three first electrical conductive type thin film transistors with bottom gates and at least one second electrical conductive type thin film transistor with a bottom gate.

17. The microarray bioprobe device integrated with an amplifier having bottom-gate thin film transistors of claim 3, wherein said amplifier comprises at least three first electrical conductive type thin film transistors with bottom gates and at least one second electrical conductive type thin film transistor with a bottom gate.

18. The microarray bioprobe device integrated with an amplifier having bottom-gate thin film transistors of claim 6, wherein said interface plate for power supply, ground and input/output has a flexible substrate and a plurality of electrical connectors penetrating therethrough.

19. The microarray bioprobe device integrated with an amplifier having bottom-gate thin film transistors of claim 7, wherein said interface plate for power supply, ground and input/output has a flexible substrate and a plurality of electrical connectors penetrating therethrough.

\* \* \* \* \*